(12) United States Patent
Moritake et al.

(10) Patent No.: US 7,541,599 B2
(45) Date of Patent: Jun. 2, 2009

(54) DOSIMETER FITTING WEAR AND BODY SURFACE EXPOSURE DOSE DISTRIBUTION MEASURING METHOD AND APPARATUS USING THE SAME

(75) Inventors: Takashi Moritake, Chiba (JP); Saburo Fujisaki, Higashiibaraki-gun (JP); Yasuhiro Koguchi, Higashiibaraki-gun (JP); Hiroshi Mizushima, Oyabe (JP); Kiyoshi Matsuno, Oyabe (JP); Takashi Uchida, Tokyo (JP)

(73) Assignees: National Institute of Radiological Sciences, Chiba (JP); Chiyoda Technol Corporation, Tokyo (JP)

( * ) Notice: Subject to any disclaimer, the term of this patent is extended or adjusted under 35 U.S.C. 154(b) by 0 days.

(21) Appl. No.: 11/884,655

(22) PCT Filed: Feb. 16, 2006

(86) PCT No.: PCT/JP2006/302750

§ 371 (c)(1),
(2), (4) Date: Aug. 20, 2007

(87) PCT Pub. No.: WO2006/090635

PCT Pub. Date: Aug. 31, 2006

(65) Prior Publication Data

US 2008/0149835 A1  Jun. 26, 2008

(30) Foreign Application Priority Data

Feb. 22, 2005 (JP) ............................. 2005-046292

(51) Int. Cl.
*G01T 1/00* (2006.01)
(52) U.S. Cl. ................................................. 250/472.1

(58) Field of Classification Search ............. 250/472.1, 250/473.1, 474.1, 475.2, 482.1, 484.3, 337; 2/456
See application file for complete search history.

(56) References Cited

U.S. PATENT DOCUMENTS 5,583,343 A * 12/1996 Dilmanian et al. ....... 250/475.2

(Continued)

FOREIGN PATENT DOCUMENTS

JP  A-59-051375  3/1984

(Continued)

OTHER PUBLICATIONS

R. Padovani, E. Quai, "Comparison of Dosimetry Approaches in Interventional Radiology" [online] (the DIMOND III research project finished Mar. 2004) [retrieved Sep. 8, 2008] <URL: http://dimond3.org/WEB_DIMOND3/Reports/WP 3/3Comparison of Dosimetry .pdf>.*

(Continued)

*Primary Examiner*—Constantine Hannaher
(74) *Attorney, Agent, or Firm*—Oliff & Berridge, PLC (57) ABSTRACT

Dosimeters 140 are housed in dosimeter housing pockets 130 of a dosimeter fitting wear including: wear main bodies 120, 150 which cover measuring positions on at least subject bodies 100, 102, and 110, and can be detachably fitted on the subject bodies, and the dosimeter housing pockets 130 provided at positions that come to the measuring positions when the wear main bodies are fitted on the subject bodies, and then the wear main bodies are fitted on the subject bodies. Thereby, a number of dosimeters can be easily fitted on or detached from the surfaces of subject bodies without hindering medical activities, and set positions of the dosimeters can be easily reproduced.

33 Claims, 10 Drawing Sheets

U.S. PATENT DOCUMENTS 6,127,685 A * 10/2000 Yoder et al. ............... 250/472.1
6,854,135 B2 * 2/2005 Jones et al. .................... 2/456
7,328,463 B2 * 2/2008 Jones et al. .................... 2/456

FOREIGN PATENT DOCUMENTS

JP   A-2003-014847   1/2003
JP   A-2003-073137   3/2003

OTHER PUBLICATIONS

M. Amano et al. "Patient Skin Dose in IVR Procedure Using Reflective Dose Measuring Film ", Academic Journal of Japanese Society of Radiological Technology, vol. 59-1, (Jan. 2003) pp. 121-129.

"Report of Research on Patient's Exposure Dose and Protection in IVR" , Academic Journal of Japanese Society of Radiological Technology, vol. 59-3, (Mar. 2003) pp. 369-381.

T. Moritake et al., "Dose Measurement on Both Patients and Operators During Neurointerventional Procedures Using Photoluminescence Glass Dosimeters," 29 AJNR 1910 (Nov.-Dec. 2008).

* cited by examiner

Front side

Fig. 13b

Back side

DOSIMETER FITTING WEAR AND BODY SURFACE EXPOSURE DOSE DISTRIBUTION MEASURING METHOD AND APPARATUS USING THE SAME

TECHNICAL FIELD

The present invention relates to a dosimeter fitting wear and body surface exposure dose distribution measuring method and apparatus using the same which realize easy measurement of exposure doses on a body surface for grasping the real condition of medical exposure and preserving it as a medical record in the medical field using a radiolucent finding.

BACKGROUND ART

IVR (interventional radiology) is for treating a human body from the inside of a blood vessel without incision of the human body by advancing a catheter inserted into the blood vessel from the femoral or forearm artery to a portion where an aneurysm or stenosis occurs in the brain or heart and placing a coil or a stent there, or advancing the catheter to a cancerous portion and dosing an embolic material or anticancer drug bringing about a high treatment effect with less invasion in comparison with other treatment methods, so that recently, IVR has produced successful results as a treatment method replacing operative treatments.

However, due to its longer X-ray fluoroscopy time and increased number of times of photography, the skin dose of a patient increased, and cases of serious skin lesions were reported.

To increase the safety and effectiveness of the IVR, it is necessary to prevent expression of deterministic effects as much as possible and lower the level of expression risk of the deterministic effect to an allowable level. Therefore, measurement of skin doses of patients, accumulation of data for a long period of time, and a proper feedback of exposure history to a medical site are necessary.

For this purpose, as described in "Patient's skin dose in IVR procedure using reflective dose measuring film," Academic Journal of Japanese Society of Radiological Technology, Vol. 59-1 (January 2003), pp. 121-129, and "Report of Research on Patient's Exposure Dose and Protection in IVR," Academic Journal of Japanese Society of Radiological Technology, Vol. 59-3 (March 2003), pp. 369-381, (1) laying of a dose measuring film between a medical bed and a patient and (2) attachment of a small-sized dosimeter to various points on the surface of a patient's body as described in, for example, Japanese Unexamined Patent Publication No. 2003-73137 (Patent Document 1), have been tried.

However, with the method (1) in which a film is laid under a patient, it is impossible to make completely closely contact with the patient's skin surface with the film, so that if the patient moves, correct values cannot be obtained. Furthermore, those measured by this method are only the X-ray doses transmitted through the film laid on the patient bed, so that the obtained values cannot accurately reflect radiation doses at various positions on the three-dimensional body surface of the patient according to X-rays that may be irradiated from various directions of the front, rear, left, and right sides.

On the other hand, the method (2) in which dosimeters are attached onto the surface of the patient's body requires a great deal of work of attaching a number of dosimeters one by one to the surface of the patient's body, and this obstructs actual medical activities, and dose measurement for a number of patients while covering the entire body surfaces in detail involves great difficulty even if it is performed as a clinical study.

At an actual medical site, the dosimeters are attached at 50 to 100 or more points on the surface of a patient's body, and it is necessary to satisfy the following requirements:

(1) Attachment of dosimeters should not obstruct treatment activities and the dosimeters can be attached and detached in about 5 minutes without pain to the patient.

(2) The dosimeters can be easily detached in case of rapid deterioration of the patient's condition.

(3) When attaching and detaching the dosimeters, they should be prevented from being broken or lost.

(4) Not only trained persons but also nurses and care staff can easily attach and detach the dosimeters.

(5) The dosimeters are radiolucent and do not obstruct treatment (X-ray fluoroscopy).

(6) The set positions of the dosimeters can be easily three-dimensionally reproduced.

(7) Doses can be easily analyzed.

(8) The dosimeters can be easily transported between a dosimeter service institution where doses are analyzed and a medical institution as a medical site.

(9) The blood and body fluids are likely to adhere to the dosimeters, and these should be prevented as much as possible from hindering all processes including dose analysis.

(10) Finally, it is necessary to analyze, accumulate, and trace several thousands through several tens of thousands of patient data, and the dosimeters can be sustainably used for the data in terms of cost as well.

(11) Furthermore, even when measurement is performed at different medical sites, it is preferable that measurement is performed at the same measuring positions in terms of data compiling.

DISCLOSURE OF THE INVENTION

An object of the present invention is to provide a dosimeter fitting wear satisfying these requirements, and body surface exposure dose measuring method and apparatus using the same.

The present invention solves the above-described problem by a dosimeter fitting wear including a wear main body which covers at least measuring positions on a subject body and is attachable to and detachable from the subject body; and dosimeter housing pockets arranged at positions that come to measuring positions when the wear main body is attached to the subject body.

The wear main body may be made of a stretchable material so as to absorb the difference in size of the subject body and make the pockets into close contact with the surface of the subject body, whereby the three-dimensional position relationship is easily reproduced.

Further, the width of at least the opening side of the dosimeter housing pocket may be formed into a shape narrowed toward the opening and/or slightly narrower than the width of the dosimeter assembly, whereby the dosimeter is prevented from falling off.

Further, the dosimeter housing pockets may be provided in a manner that the distance between adjacent dosimeters becomes experientially 100 millimeters or less so that any one of dosimeters always enters the field of irradiation during a treatment with unfixed irradiation directions and irradiation fields, whereby the dosimeters can be prevented as much as possible from missing the field of X-ray irradiation.

Further, the dosimeter housing pockets may be made of a stretchable material so as to prevent the dosimeters from falling off.

Further, the dosimeter housing pockets may be attached with position IDs corresponding to measuring positions to make identification of the measuring positions easy and realize efficient work.

Further, the dosimeter housing pockets may be three-dimensionally arranged along the subject body surface so that the dosimeters are prevented as much as possible from missing the field of X-ray irradiation.

Further, the wear main body may be formed into a cap shape covering the head of the subject body so as to become applicable to a treatment of the head.

Further, a part of the dosimeter housing pockets may be positioned so as to cover the eyes of the subject body to accurately detect doses on the eyeballs.

Further, the cap-shaped wear main body may include a semispherical portion covering the head of the subject body, an eye-fitting belt which has both ends held on the semispherical portion and can be separable at the center, an apron hung rearward from the semispherical portion for covering the nape of the neck of the subject body, and a neck-fitting belt which has both ends held on the apron and can be wound around the cervix of the subject body.

Further, a stretch-restorable core material may be fitted near the connecting portions between the eye-fitting belt and the semispherical portion so as to prevent the eye-fitting belt from being elongated and deformed due to repeated fitting.

Further, the wear main body may be formed into a T-shirt shape or a vest shape covering at least the chest of the subject body so as to become applicable to a treatment of the heart and lungs.

Further, a part of the dosimeter housing pockets may be positioned near the thyroid gland of the subject body so that the exposure dose of the thyroid gland is accurately detected.

Further, the T-shirt-shaped or vest-shaped wear main body may include a trunk portion that is for covering the chest of the subject body and can be wound around the trunk of the subject body while separated at the front chest, arm portions that have upper ends held on the trunk portion and can be wound around the brachial regions of the subject body while separated at the inner sides of the brachia, and a neck-fitting belt that has both ends held on the trunk portion and can be wound around the cervix of the subject body.

The present invention provides a body surface exposure dose distribution measuring method in which dosimeters are housed in the dosimeter housing pockets of the dosimeter fitting wear and fitted on the subject body.

Further, the dosimeters may be housed in sealing bag-like members in an assembly state and housed in the dosimeter housing pockets so as to be prevented from being contaminated by blood and body fluids.

The present invention provides a body surface exposure dose distribution measuring apparatus including the above-described dosimeter fitting wear and dosimeters to be housed in the dosimeter housing pockets of the dosimeter fitting wear.

Further, element IDs to the dosimeters for identifying measuring positions may be attached so that identification of the dosimeters after being detached from the wear is made easy and efficient work is realized.

In addition, the present invention provides a body surface exposure dose distribution measuring method in which a dosimeter fitting wear housing initialized dosimeters in pockets is delivered from a dosimeter service institution to a medical institution, fitted on a subject body and used at the medical institution, and then returned to and recovered by the dosimeter service institution while the dosimeters are left housed in the pockets, measured values of the dosimeters are read at the dosimeter service institution and the medical institution is informed of these, and the measured values of the dosimeters read at the dosimeter service institution are stored at an archives institution.

Further, measured values of the dosimeters may be processed into an exposure dose distribution map corresponding to measuring positions and the medical institution is informed of it from the dosimeter service institution, whereby grasping of the exposure dose distribution is made easy.

In addition, the present invention provides a body surface exposure dose distribution indication apparatus including a recording means for recording exposure dose distributions measured by the above-described method based on subject IDs, a summing means for summing exposure dose distributions recorded based on the same position IDs, and a display means for displaying a summed total exposure dose distribution.

According to the present invention, excellent effects are obtained that, by fitting the dosimeter fitting wear housing in advance dosimeters in the dosimeter housing pockets on a subject body, without hindering treatment activities and without causing the subject body pain, the dosimeters can be easily attached and detached in a short time. In addition, three-dimensional set positions of the dosimeters can be easily reproduced, so that summing is easy and data reliability is high. Furthermore, the dosimeters can be easily transported while left housed in the pockets of the wear. In addition, a doctor performs a treatment while avoiding excessive concentration of radiation upon grasping past exposure dose distributions, whereby skin lesions can be prevented.

BEST MODE FOR CARRYING OUT THE INVENTION

Hereinafter, embodiments of the present invention will be described in detail with reference to the drawings.

Figure 1:
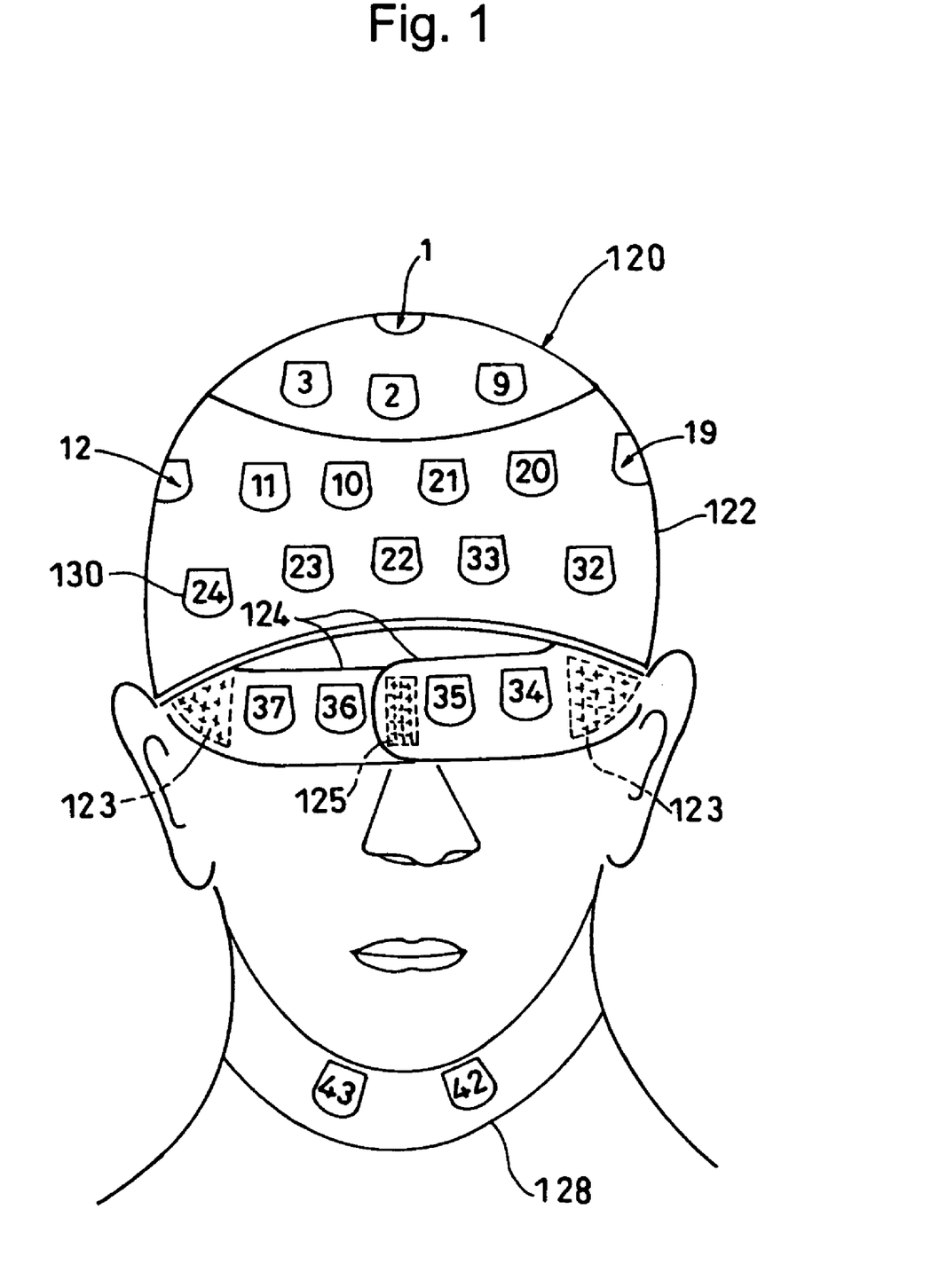
FIG. 1 is a front view showing a state that a first embodiment of invention suitable for the head exposure dose distribution measurement is fitted on the head of a patient.
Figure 2:
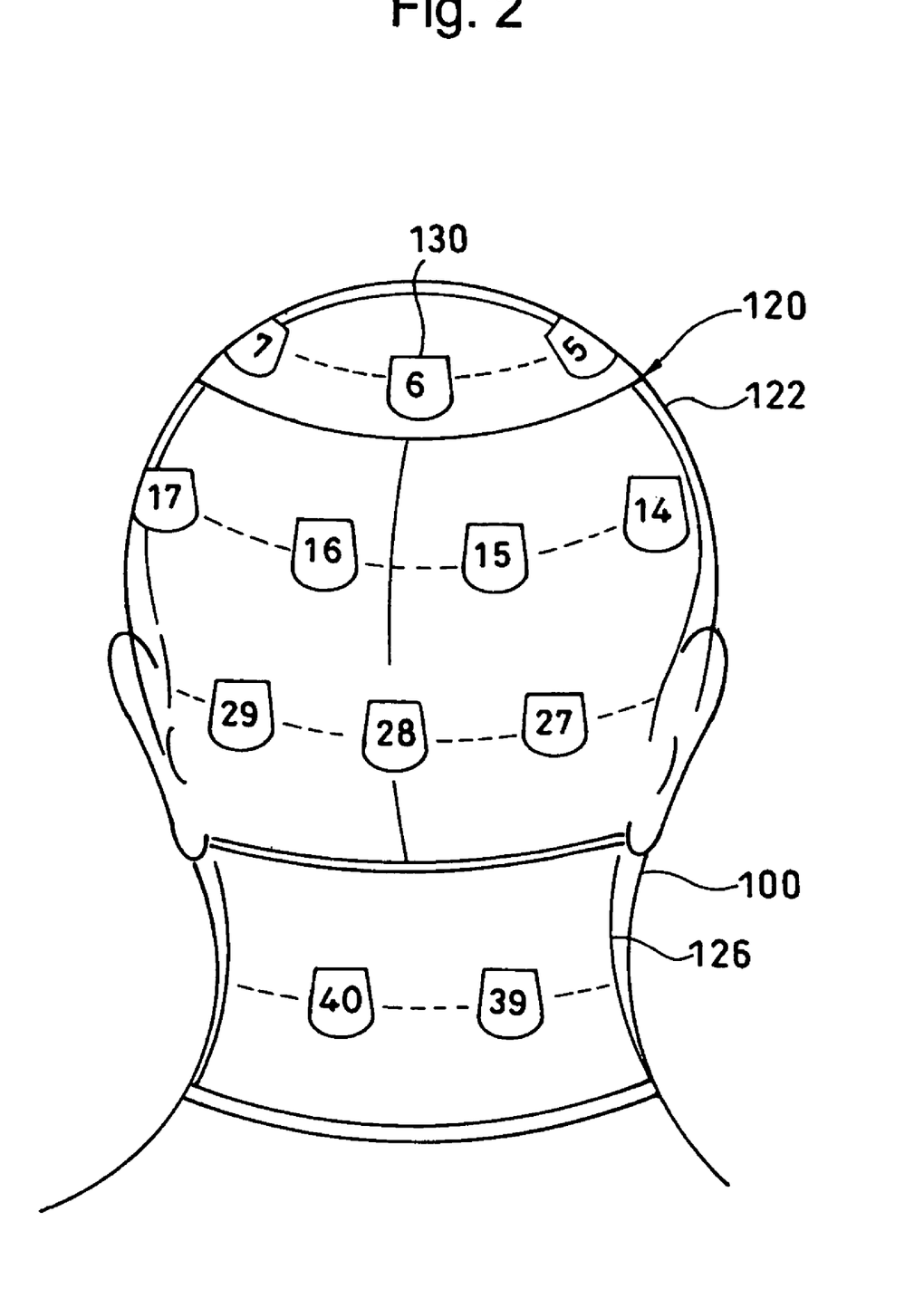
FIG. 2 is a back view of the same.
Figure 3:
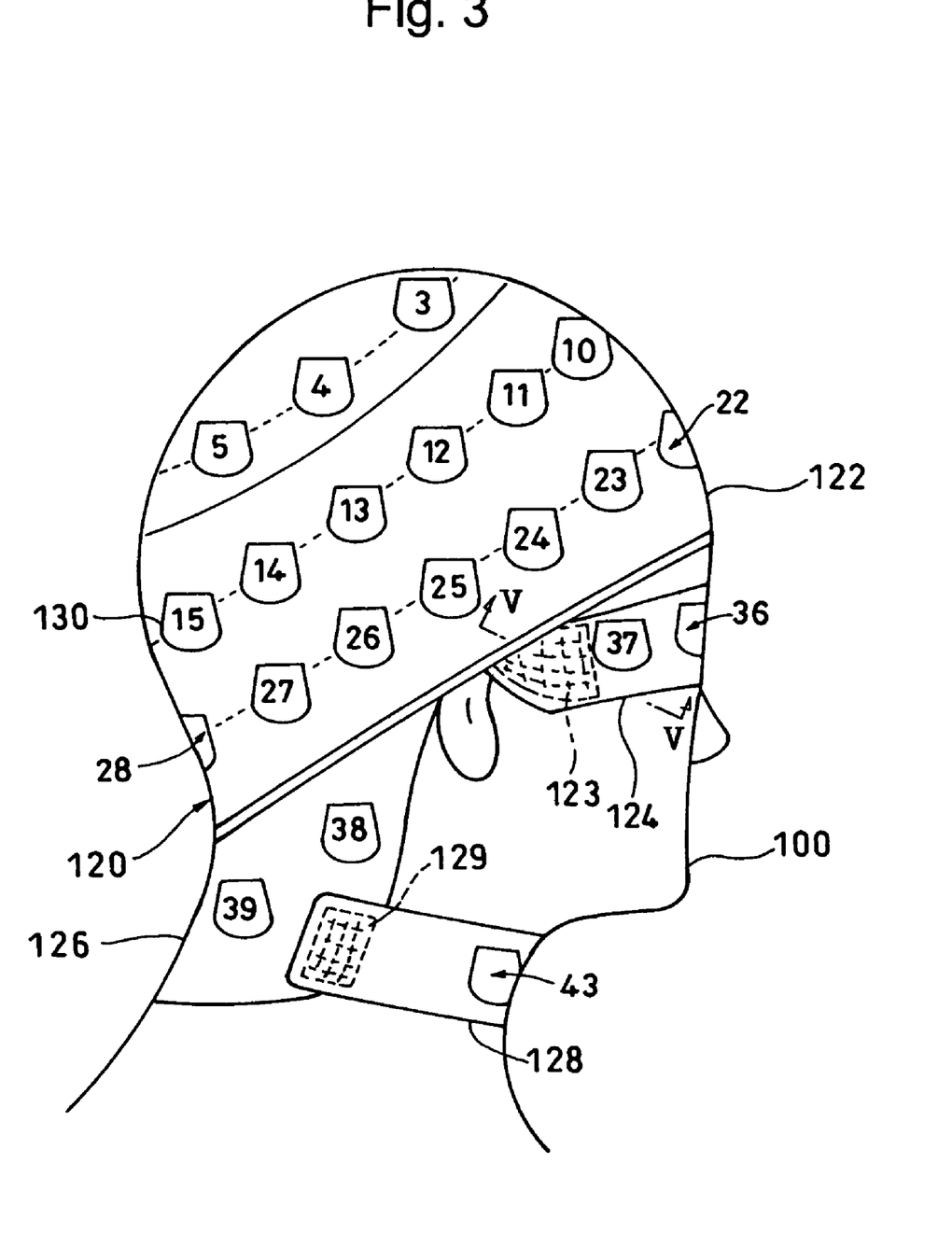
FIG. 3 is a right side view of the same.
Figure 4:
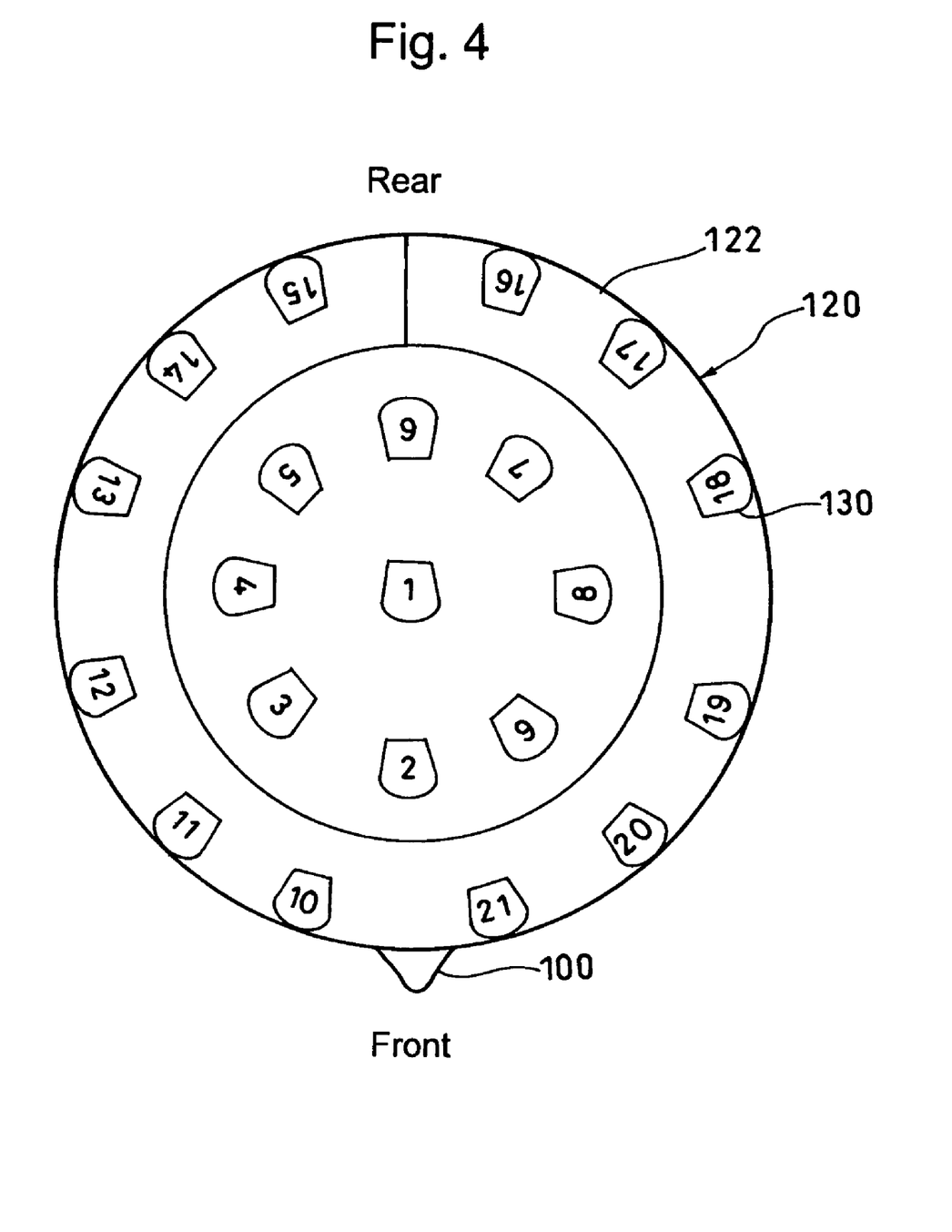
FIG. 4 is a plan view of the same.

A first embodiment of the present invention is suitable for exposure dose distribution measurement of the head of a patient, and includes, as shown in FIG. 1 (front view showing a fitting state on the head of a patient), FIG. 2 (back view of the same), FIG. 3 (right side view of the same), and FIG. 4 (plan view of the same), a cap-shaped wear main body 120 which covers the head 100 of a patient and can be detachably fitted on the head and a number (forty-three in this embodiment) of dosimeter housing pockets (also referred to as pockets, simply) 130 arranged at positions that come to measuring positions on the outer side of the wear main body 120 when fitted on the head of the patient.

The wear main body 120 includes a semispherical portion 122 which is in a simple semispherical shape like a swimming cap and covers the head of a patient, an eye-fitting belt 124 which has both ends held on the semispherical portion 122 and is separable at the center, an apron 126 (see FIG. 2 and FIG. 3) hung rearward from the semispherical portion 122 for covering the nape of the neck of the patient, and a neck-fitting belt 128 which has both ends held on the apron 126 and can be wound around the cervix of the patient.

At the separating portion on the front surface of the eye-fitting belt 124, as shown in FIG. 1, a surface fastener 125 is arranged so that the length is easily adjustable according to the head size of the patient.

Figure 5:
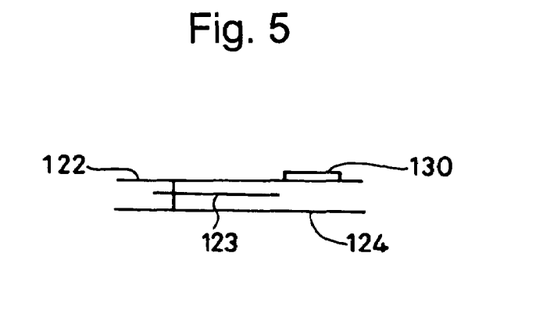
FIG. 5 is a sectional view showing connection between a semispherical portion and an eye-fitting belt of the same.

Into the connecting portions between the eye-fitting belt 124 and the semispherical portion 122, to prevent elongating deformation of the eye-fitting belt 124 due to repeated fitting, as shown in the section of FIG. 5, a core material with high stretch-restorability (mesh stretchy fiber such as a power net) 123 is sewn.

Also, into an end of the neck-fitting belt 128, as shown in FIG. 3, a surface fastener 129 is arranged so that the belt is easily adjustable according to the neck of the patient.

Figure 6:
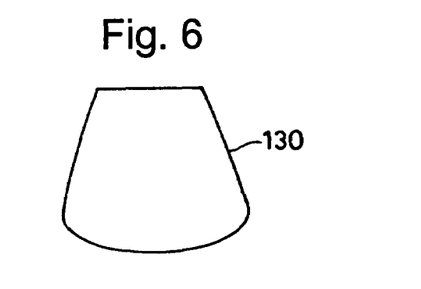
FIG. 6 is a front view showing a shape of a dosimeter housing pocket of the same.

The pocket 130 is formed into a pot-like shape whose opening is narrowed as shown in FIG. 6 to prevent a dosimeter from easily falling off. By forming the width of the opening side slightly narrower than the width of a dosimeter assembly, the dosimeter becomes more difficult to fall off. This pocket 130 is constant in size, flat so as not to hinder the stretching of the wear main body, cut by a laser so as to prevent fraying from the end of the texture, and sewn by an automatic machine. To make it easy to put the dosimeter in the pocket, the positions of the pockets 130 provided on the belts 124 and 128 are A (about 2 millimeters) lower than the upper edges of the belts 124 and 128.

The pockets 130 are attached with, for example, numbers 1 to 43 as position IDs as illustrated so that the positions of the pockets can be easily identified from the numbers.

Herein, the pockets on the semispherical portion 122, for example, pocket numbers 1 through 33 are substantially evenly three-dimensionally arranged so that the distance between pockets adjacent to each other when fitted becomes 100 millimeters or less. This is determined by considering that an irradiation spot diameter in recent treatments and examinations are experientially not less than 120 millimeters.

Figure 7:
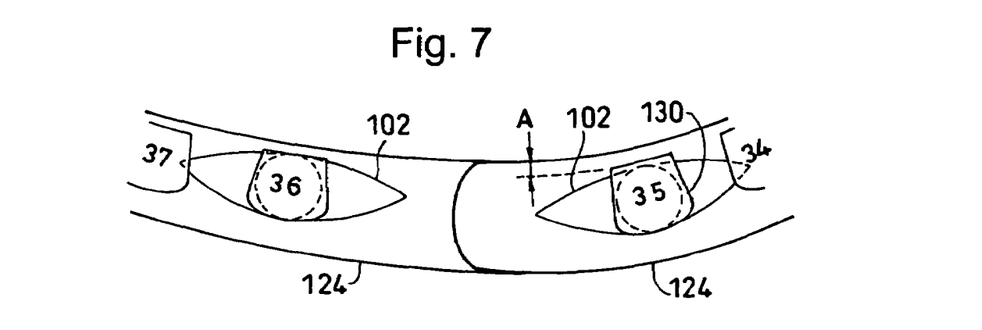
FIG. 7 is a front view showing a pocket attaching state to the eye-fitting belt of the same.

As shown in FIG. 7, among four pockets 34 through 37 on the eye-fitting belt 124, for example, the pocket numbers 35 and 36 are positioned just above the eyes 102 of the patient, and the pocket numbers 34 and 37 are positioned at the ends of the eyes 102.

On the apron 126, as shown in FIG. 2 and FIG. 3, two pockets for measuring the portion of the carotid artery, for example, the pocket numbers 38 and 41, and two pockets for measuring the nape of the neck, for example, the pocket numbers 39 and 40 are provided.

Figure 8:
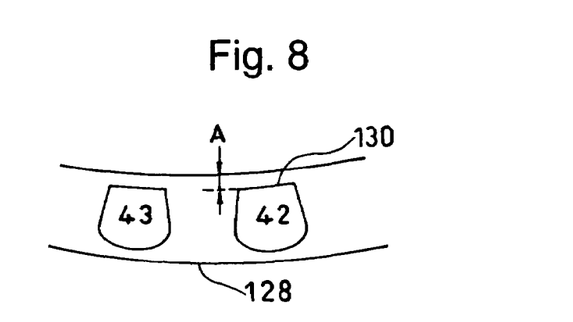
FIG. 8 is a front view showing a pocket attaching state to a neck-fitting belt of the same.

The pockets on the neck-fitting belt 128, for example the pocket numbers 42 and 43, can be positioned near the thyroid gland as shown in FIG. 1.

Figure 9:
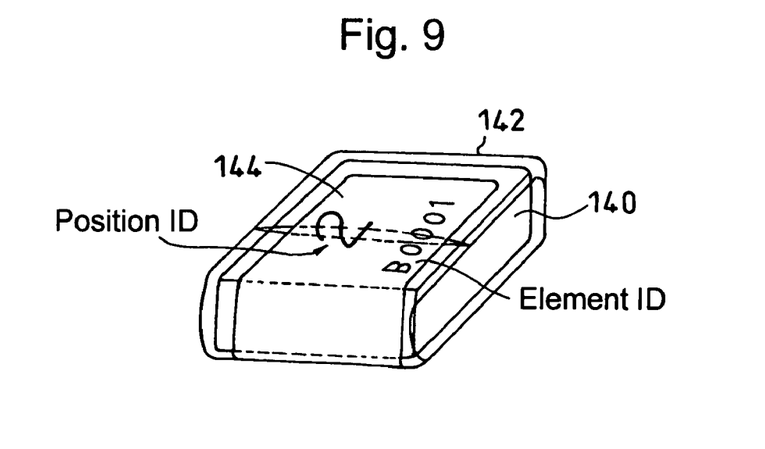
FIG. 9 is a perspective view showing a dosimeter before inserted in a pocket of the same.
Figure 10:
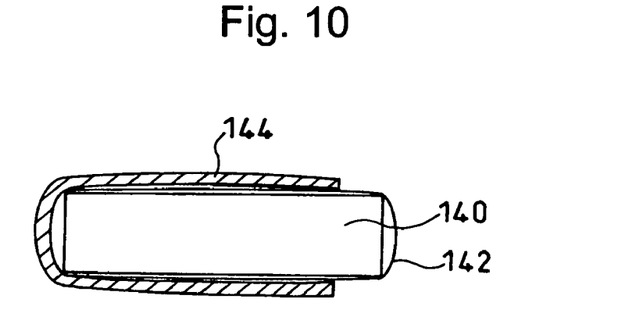
FIG. 10 is a sectional view of the same.

As shown in FIG. 9 (a perspective view) and FIG. 10 (a sectional view), in each pocket, for example, a photoluminescence glass dosimeter 140 of 1.0 cm square and 0.8 mm thickness made of transparent phosphate glass containing silver dispersed or the like, as described in Patent document 1, is inserted in the pocket 130 in an assembly state that the dosimeter is put in a polyethylene or vinyl sealing bag 142 for preventing contamination by blood and body fluids and attached with a rectangular seal 144 having fitting position and element IDs printed thereon, folded and affixed in a C shape.

Figure 11:
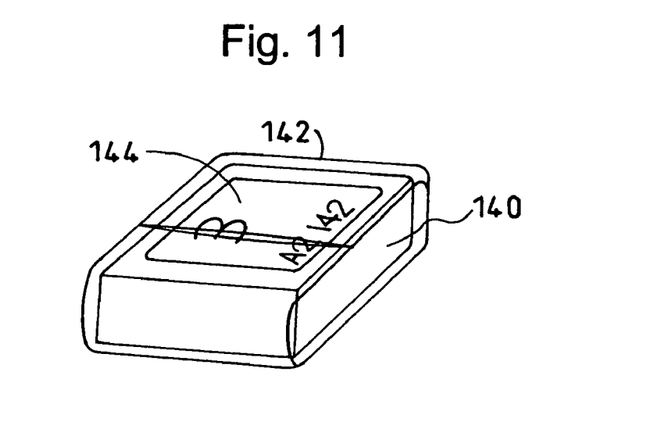
FIG. 11 is a perspective view showing a variation of a dosimeter before inserted in a pocket of the same.

As in the variation shown in FIG. 11, it is also possible that a rectangular seal 144 is affixed onto the dosimeter 140 and the dosimeter is put inside the sealing bag 142 so that the seal 144 is also prevented from being contaminated by blood and body fluids.

To prevent the wear main body 120 and the pockets 130 from being displaced due to the positions of the dosimeters 140 put into the pockets 130 and the size and the shape of the head 100 of the patient, the wear main body 120 and the pockets 130 are made of a material stretchable in all directions such as polyester, polyurethane, nylon, or the like having stretchability and strength for, for example, swimming suits (sports wear) and sewn in a manner suitable for the texture by using a stretchable sewing thread. As the material stretchable in all directions, for example, unwoven fabric, or non-stretchable natural fabrics such as paper, cotton, and silk which are reticulated can also be used. As the stretchable sewing thread, for example, a woolly nylon, polyester, or polyurethane thread can be used.

Next, a second embodiment of the present invention in a T-shirt shape suitable for chest exposure dose distribution measurement will be described in detail.

Figure 12A:
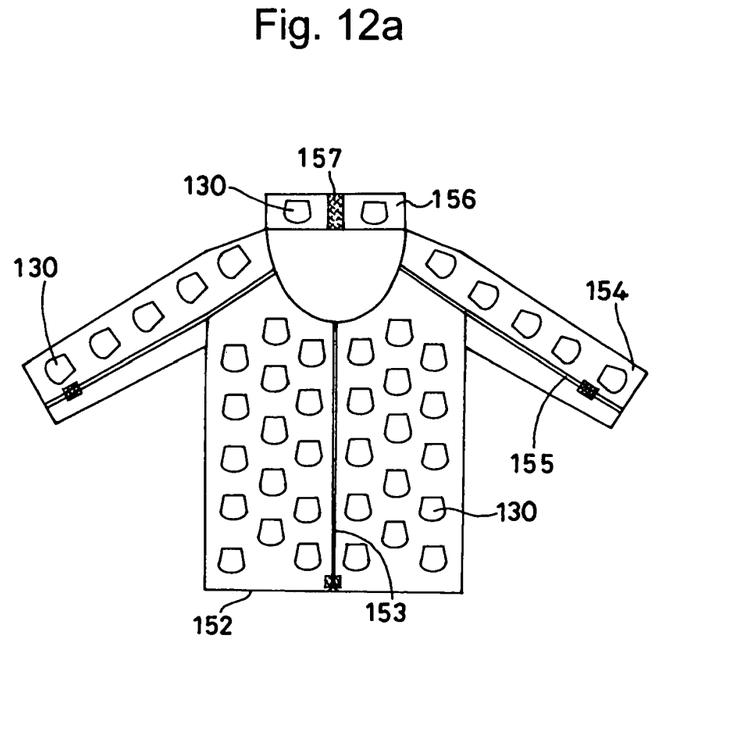
FIG. 12a and FIG. 12b are a front view and a developed view of a second embodiment of the present invention in a T-shirt shape suitable for chest exposure dose distribution measurement.
Figure 12B:
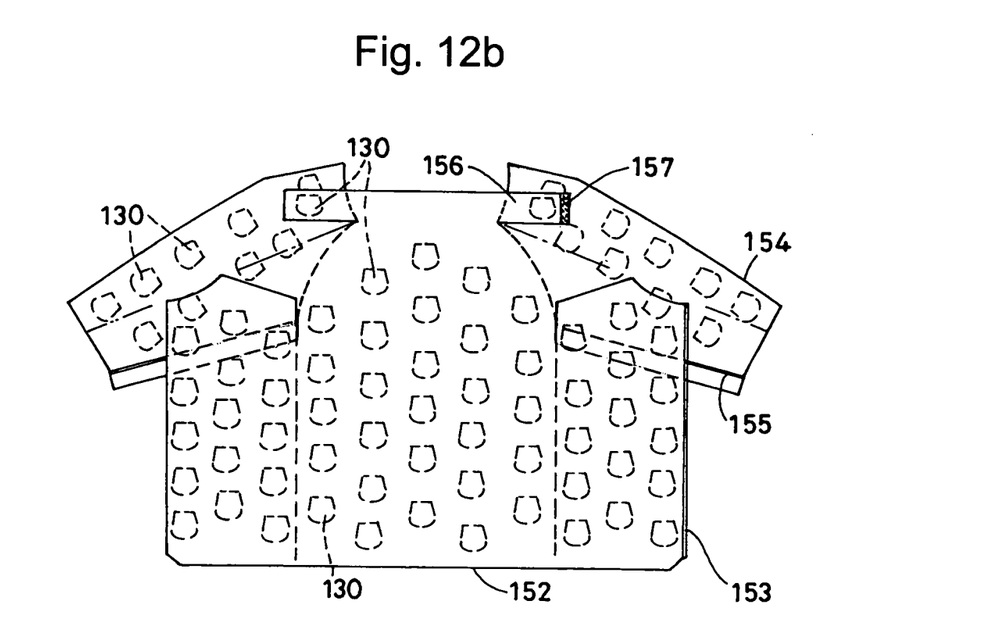
Figure 13A:
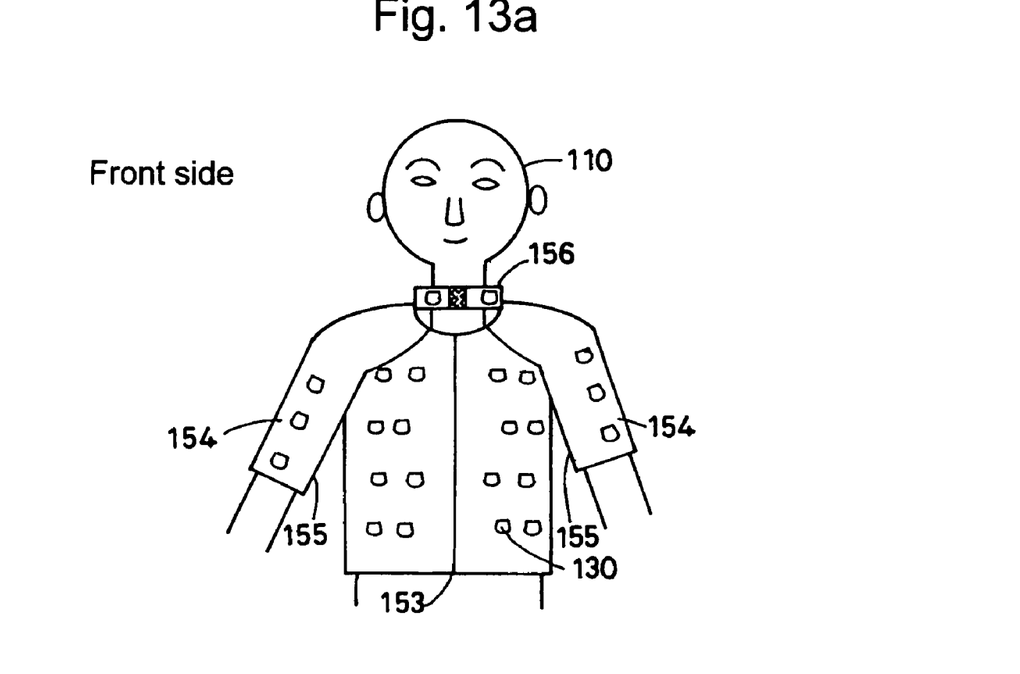
FIG. 13a and FIG. 13b are a front view and a back view showing a fitting state on a patient of the same.
Figure 13B:
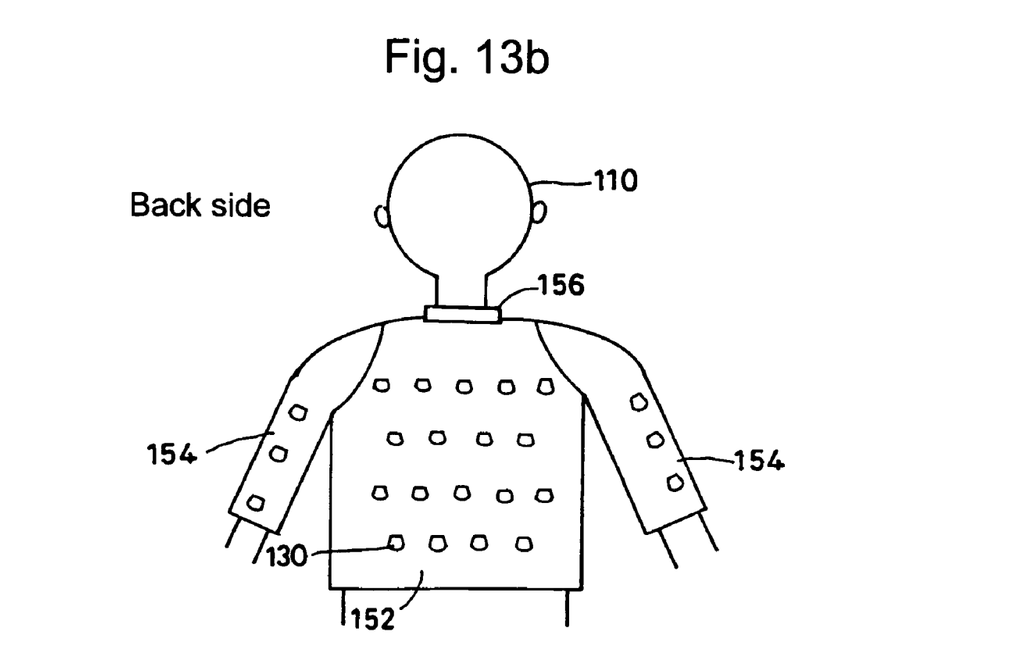

The T-shirt-shaped wear main body 150 of this embodiment includes, as shown in FIG. 12 (FIG. 12a front view and FIG. 12b developed view before being fitted on a patient) and FIG. 13 (FIG. 13a front view and FIG. 13b back view showing a fitted state on a patient), a trunk portion 152 which is for covering the chest of the patient and can be wound around the trunk of the body of the patient by being separated at the front chest, arm portions 154 which are integrated with the trunk portion 152 and can be wound around the brachia 110 of the patient by being separated on the inner sides of the brachia, a neck-fitting belt 156 which has both ends held on the trunk portion 152 and can be wound around the cervix of the patient, and dosimeter housing pockets 130 similar to those of the first embodiment provided on the outer sides of the respective portions (in particular, the back, the trunk side surfaces, and brachia outer surfaces).

The trunk portion 152 is set in length so as to cover from the neck as an upper limit to the rib lower edge as a lower limit.

The trunk portion 152, the arm portions 154, and the neck-fitting belt 156 are provided with surface fasteners 153, 155, and 157 for fastening these wound around the patient, respectively.

When fitting on the patient, the wear main body 150 housing dosimeters is laid on a bed by turning the pockets 130 to the outer side (bed side), and the patient is laid on the wear main body and then the wear is wound around the trunk, brachia, and cervix and fastened by the surface fasteners.

Other points in the description are the same as in the first embodiment and are omitted herein.

Figure 14A:
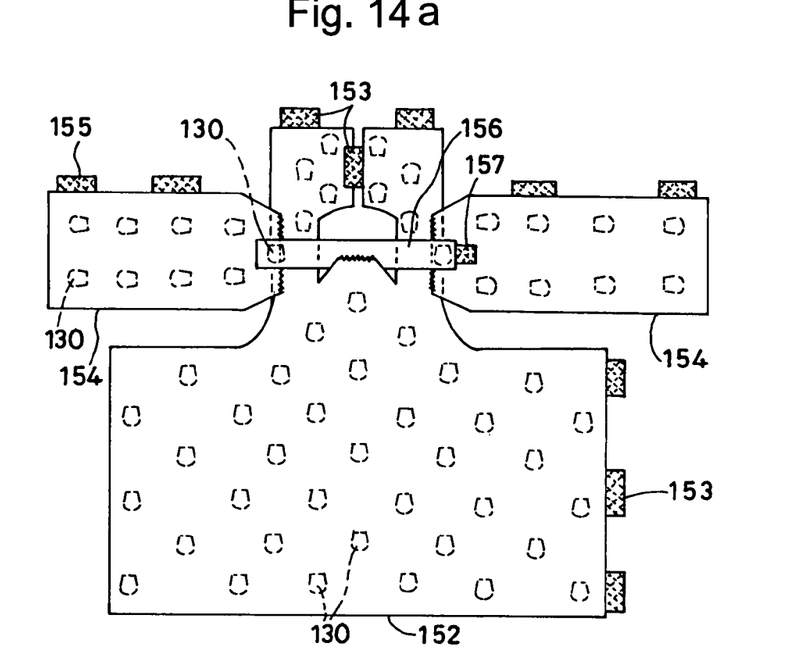
FIG. 14a and FIG. 14b are a developed view and a front view of a third embodiment of the present invention in a vest shape suitable for chest exposure dose distribution measurement.
Figure 14B:
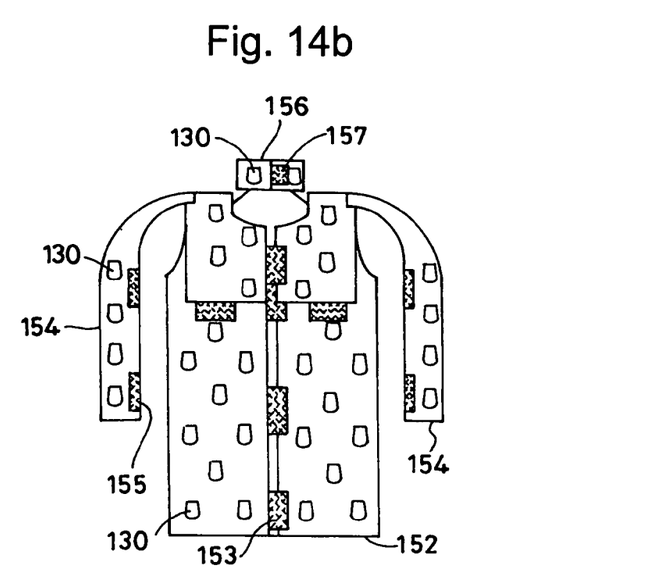

In this embodiment, the trunk portion 152 and the arm portions 154 are integrated, so that reproducibility of the dosimeter positions to be housed in the pockets of the arm portions 154 is high. As in the third embodiment shown in FIG. 14, the vest shape including separated arm portions 154 is also allowed.

In any of the first through third embodiments, as the wear main body 120 or 150, varied sizes for children or adults can be prepared. Instead of the surface fasteners, resin-made fasteners or tape-like buttons may also be used.

Figure 15:
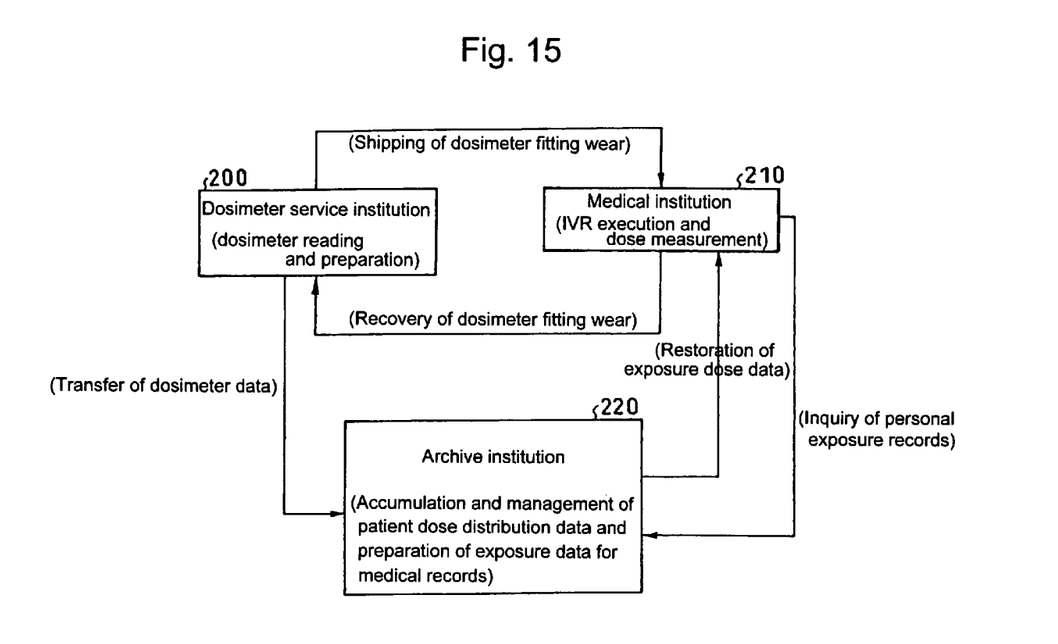
FIG. 15 is a block diagram showing a data processing method of dosimeters.
Figure 16:
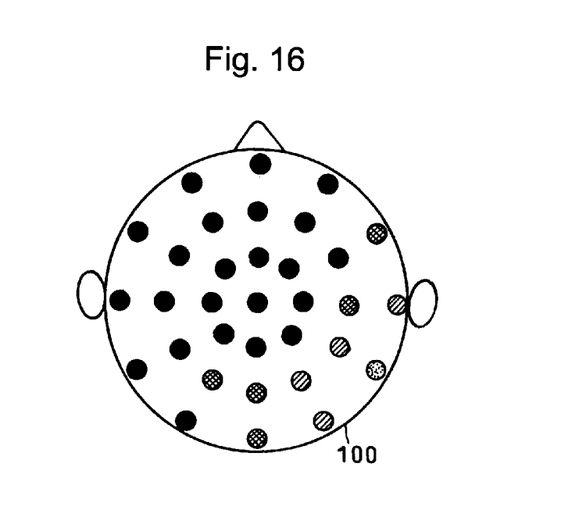
FIG. 16 is a diagram showing an example of dose distribution data of the same.

When performing measurement, as shown in FIG. 15, dosimeter fitting wears 120 and 150 housing dosimeters 140 initialized at the dosimeter service institution 200 in the pockets 130 are delivered to the medical institution 210 from the dosimeter service institution 200, and the dosimeter fitting wears 120 and 150 after being fitted and used on the patient at the medical institution 210 are returned to and recovered by the dosimeter service institution 200 together with a patient (subject) ID, and the dosimeters 200 are read at the dosimeter service institution 200 and the results of readout of the measured values are drawn in, for example, the form of a dose distribution map indicating doses corresponding to the respective position IDs as shown in FIG. 16, and the medical institution 210 can be informed of this.

At this time, it is desired that at the archives institution 220, the patient dose distribution data is accumulated and managed, and patient exposure database is created as described below.

That is, patient dose distribution data measured every exposure of a certain patient are corrected and recorded on a server of the archive institution 220 together with the medical institutions where the patient was subjected to exposure, exposure dates, and irradiation methods, etc., for each patient ID, and patient exposure database is created. In the database, exposure doses of respective position IDs in these patient exposure data are summed according to a predetermined program and total exposure dose distribution data of the patient is also created in advance. Thereby, when the patient visits the medical institution 210, at the request of the medical institution 210, these data can be transmitted through a communications line. It is also possible that the total exposure dose distribution data is created by a computer of the medical institution 210 by transmitting each patient exposure data and a predetermined program to the medical institution 210 through a communications line.

At the medical institution 210, obtained total exposure dose distribution data is indicated by being drawn on a monitor or printed and observed, or exposure dose distribution data of each exposure is observed in the same manner, and the irradiation method and positions of this time can be examined, explained to the patient, and added to the medical records of the patient.

The archive institution 220 is a public institution, desirably.

Thus, the actual conditions of patient exposure in IVR or the like can be easily known. Furthermore, by tracing the harm case caused by radiation on a patient basis, large-scale epidemiological investigation results are finally obtained.

Furthermore, if the patient exposure data is fed back to the medical institution, not only can complete control of patient radiation exposure be realized but also the technique on the doctor side for reducing the exposure dose can be improved by using the data for training. A doctor who performs the IVR can obtain clear-cut information on side effects by knowing patient exposure data of the case the doctor is concerned with on a routine basis. From this information, previous to performing the IVR in actuality, it becomes possible for the doctor to explain the risk and benefit to a patient based on his/her own experiments, and this helps the doctor to build a satisfactory doctor-patient relationship.

In this embodiment, a photoluminescence glass dosimeter is used which uses a radio photoluminescence (RPL) phenomenon in which luminescence is generated when glass irradiated with radiation is exposed to ultraviolet rays, so that it is radiolucent and can be used repeatedly. The type of the dosimeter is not limited to this, all radiation meters capable of measuring X-rays such as a thermal luminescence dosimeter (TLD) using a thermal luminescence material (TL material) which is a luminescent (thermal luminescent) material which emits light after irradiated with radiation and heated, and whose luminescence amount is in proportion to a radiation absorbed dose, an OSL (Optically Stimulated Luminescence) dosimeter using luminescence (optically stimulated luminescence) which appears when an energy charged material due to interaction with radiation is irradiated with light, a film type dosimeter, an imaging plate which utilizes the phenomenon that radiation energy is temporarily charged and then luminescence is emitted due to excitation of heat or light (photostimulated luminescence), a chemical dosimeter (iron, cerium, alanine), an NaI (Tl) scintillation counter, a semiconductor detector, an Si (Li) detector, an Si surface barrier detector, an ionization chamber, a proportional counter, a Geiger-Mueller counter (GM counter), and the like.

In the embodiments described above, the present invention is applied to IVR of human bodies, however, without limiting to this, the present invention is also applicable to exposure dose distribution measurement of general living bodies including animals and plants and non-living bodies.

INDUSTRIAL APPLICABILITY

The present invention can be used for grasping the actual conditions of medical exposure and remaining it as medical records in the medical field using a radiolucent finding.

The invention claimed is:

1. A dosimeter fitting wear comprising:
    a wear main body which can be fitted on a patient to be diagnosed and/or treated with close contact and covers at least a plurality of measuring positions on the patient; and
    a plurality of dosimeter housing pockets arranged at positions that come to the measuring positions when the wear main body is fitted on the patient, wherein
    the wear main body is formed into a cap shape which covers the head of the patient, the wear main body comprising:
    a semispherical portion which covers the head of the patient with close contact;
    an eye-fitting belt which has both ends held on the semispherical portion and is separable at the center;
    an apron hung rearward from the semispherical portion, for covering the nape of the neck of the patient; and
    a neck-fitting belt which has both ends held on the apron and can be wound around the cervix of the patient to make close contact with the patient.

2. The dosimeter fitting wear according to claim 1, wherein the wear main body is made of a stretchable material.

3. The dosimeter fitting wear according to claim 1, wherein the widths on at least the opening sides of the dosimeter housing pockets are narrowed.

4. The dosimeter fitting wear according to claim 1, wherein the widths on at least the opening sides of the dosimeter housing pockets are formed to be slightly narrower than the width of a dosimeter assembly.

5. The dosimeter fitting wear according to claim 1, wherein the dosimeter housing pockets are provided so that the distance between dosimeters adjacent to each other becomes 100 millimeters or less.

6. The dosimeter fitting wear according to claim 1, wherein the dosimeter housing pockets are made of a stretchable material.

7. The dosimeter fitting wear according to claim 1, wherein the dosimeter housing pockets are attached with position IDs corresponding to measuring positions.

8. The dosimeter fitting wear according to claim 1 wherein the respective dosimeter housing pockets are three-dimensionally arranged so that they fit the subject body surface.

9. The dosimeter fitting wear according to claim 1, wherein a stretch-restorable core material is fitted near a connecting portion between the eye-fitting belt and the semispherical portion.

10. A dosimeter fitting wear comprising:
a wear main body which can be fitted on a patient to be diagnosed and/or treated with close contact and covers at least a plurality of measuring positions on the patient; and
a plurality of dosimeter housing pockets arranged at positions that come to the measuring positions when the wear main body is fitted on the patient, wherein
the wear main body is formed into a T-shirt shape or a vest shape which covers at least the chest of the patient, the wear main body comprising:
a trunk portion which can be wound around the trunk of the patient by being separated at the front chest, for covering the chest of the patient with close contact; and
arm portions which can be wound around the brachia of the patient by being separated on the inner sides of the brachia, having upper ends of each arm portion held on the trunk portion.

11. The dosimeter fitting wear according to claim 10, wherein a part of the dosimeter housing pockets is positioned near the thyroid gland of the patient.

12. The dosimeter fitting wear according to claim 10, further comprising
a neck-fitting belt which can be wound around the cervix of the patient, having both ends held on the trunk portion.

13. The dosimeter fitting wear according to claim 10, wherein the wear main body is made of a stretchable material.

14. The dosimeter fitting wear according to claim 10, wherein the widths on at least the opening sides of the dosimeter housing pockets are narrowed.

15. The dosimeter fitting wear according to claim 10, wherein the widths on at least the opening sides of the dosimeter housing pockets are formed to be slightly narrower than the width of a dosimeter assembly.

16. The dosimeter fitting wear according to claim 10, wherein the dosimeter housing pockets are provided so that the distance between dosimeters adjacent to each other becomes 100 millimeters or less.

17. The dosimeter fitting wear according to claim 10, wherein the dosimeter housing pockets are made of a stretchable material.

18. The dosimeter fitting wear according to claim 10, wherein the dosimeter housing pockets are attached with position IDs corresponding to measuring positions.

19. The dosimeter fitting wear according to claim 10, wherein the respective dosimeter housing pockets are three-dimensionally arranged so that they fit the patient body surface.

20. A body surface exposure dose distribution measuring method comprising:
fitting dosimeter fitting wear on a patient; and
using dosimeters to measure body surface exposure dose distribution, wherein the dosimeters are housed in dosimeter housing pockets of the dosimeter fitting wear, the dosimeter fitting wear comprising:
a wear main body which can be fitted on the patient to be diagnosed and/or treated with close contact and covers at least a plurality of measuring positions on the patient; and
a plurality of dosimeter housing pockets arranged at positions that come to the measuring positions when the wear main body is fitted on the patient, wherein the wear main body is formed into a cap shape which covers the head of the patient, the wear main body comprising:
a semispherical portion which covers the head of the patient with close contact;
an eye-fitting belt which has both ends held on the semispherical portion and is separable at the center;
an apron hung rearward from the semispherical portion, for covering the nape of the neck of the patient; and
a neck-fitting belt which has both ends held on the apron and can be wound around the cervix of the patient to make close contact with the patient.

21. The body surface exposure dose distribution measuring method according to claim 20, wherein the dosimeters are attached with element IDs for identifying measuring positions.

22. The body surface exposure dose distribution measuring method according to claim 20, wherein the dosimeters are housed in the dosimeter housing pockets in an assembly state that the dosimeters are housed in sealing bag-like members.

23. A body surface exposure dosed distribution measuring method comprising:
fitting dosimeter fitting wear on a patient; and
using dosimeters to measure body surface exposure dose distribution, wherein the dosimeters are housed in dosimeter housing pockets of the dosimeter fitting wear, the dosimeter fitting wear comprising:
a wear main body which can be fitted on the patient to be diagnosed and/or treated with close contact and covers at least a plurality of measuring positions on the patient; and
a plurality of dosimeter housing pockets arranged at positions that come to the measuring positions when the wear main body is fitted on the patient, wherein the wear main body is formed into a T-shirt shape or a vest shape which covers at least the chest of the patient, the wear main body comprising:
a trunk portion which can be wound around the trunk of the patient by being separated at the front chest, for covering the chest of the patient with close contact; and
arm portions which can be wound around the brachia of the patient by being separated on the inner sides of the brachia, having upper ends held on the trunk portion.

24. A body surface exposure dose distribution measuring method according to claim 23, wherein the dosimeters are radiolucent and do not obstruct treatment.

25. The body surface exposure dose distribution measuring method according to claim 23, wherein the dosimeters are attached with element IDs for identifying measuring positions.

26. The body surface exposure dose distribution measuring method according to claim 23, wherein the dosimeters are housed in the dosimeter housing pockets in an assembly state that the dosimeters are housed in sealing bag-like members.

27. A body surface exposure dose distribution measuring apparatus comprising:
   dosimeter fitting wear comprising:
      a wear main body which can be fitted on a patient to be diagnosed and/or treated with close contact and covers at least a plurality of measuring positions on the patient; and a plurality of dosimeter housing pockets arranged at positions that come to the measuring positions when the wear main body is fitted on the patient, wherein the wear main body is formed into a cap shape which covers the head of the patient, the wear main body comprising:
         a semispherical portion which covers the head of the patient with close contact; an eye-fitting belt which has both ends held on the semispherical portion and is separable at the center;
         an apron hung rearward from the semispherical portion, for covering the nape of the neck of the patient; and
         a neck-fitting belt which has both ends held on the apron and can be wound around the cervix of the patient to make close contact with the patient; and
      dosimeters to be housed in dosimeter housing pockets of the dosimeter fitting wear.

28. The body surface exposure dose distribution measuring apparatus according to claim 27, wherein the dosimeters are attached with element IDs for identifying measuring positions.

29. A body surface exposure dose distribution measuring apparatus comprising:
   dosimeter fitting wear comprising:
      a wear main body which can be fitted on a patient to be diagnosed and/or treated with close contact and covers at least a plurality of measuring positions on the patient; and a plurality of dosimeter housing pockets arranged at positions that come to the measuring positions when the wear main body is fitted on the patient, wherein the wear main body is formed into a T-shirt shape or a vest shape which covers at least the chest of the patient, the wear main body comprising:
         a trunk portion which can be wound around the trunk of the patient by being separated at the front chest, for covering the chest of the patient with close contact; and
         arm portions which can be wound around the brachia of the patient by being separated on the inner sides of the brachia, having upper ends held on the trunk portion; and
      dosimeters to be housed in dosimeter housing pockets on the dosimeter fitting wear.

30. The body surface exposure dose distribution measuring apparatus according to claim 29, wherein the dosimeters are attached with element IDs for identifying measuring positions.

31. A body surface exposure dose distribution indication apparatus comprising:
   a recording means for recording exposure dose distributions measured by a body surface exposure dose distribution measuring method, wherein dosimeters are housed in dosimeter housing pockets of dosimeter fitting wear, the dosimeter fitting wear comprising:
      a wear main body which can be fitted on a patient to be diagnosed and/or treated with close contact and covers at least a plurality of measuring positions on the patient; and a plurality of dosimeter housing pockets arranged at positions that come to the measuring positions when the wear main body is fitted on the patient, wherein the wear main body is formed into a cap shape which covers the head of the patient, the wear main body comprising:
         a semispherical portion which covers the head of the patient with close contact; an eye-fitting belt which has both ends held on the semispherical portion and is separable at the center;
         an apron hung rearward from the semispherical portion, for covering the nape of the neck of the patient; and
         a neck-fitting belt which has both ends held on the apron and can be wound around the cervix of the patient to make close contact with the patient and the dosimeter fitting wear is fitted on the patient based on subject IDs;
      a summing means for summing exposure dose distributions recorded based on the same position ID; and
      a display means for displaying the summed total exposure dose distribution.

32. A body surface exposure dose distribution measuring method, comprising:
   delivering a dosimeter fitting wear including pockets in which initialized dosimeters are housed from a dosimeter service institution to a medical institution;
   returning and recovering the dosimeter fitting wear after being fitted on a patient to be diagnosed and/or treated with close contact and used at the medical institution while the dosimeters are left housed in the pockets, to the dosimeter service institution; and
   informing the medical institution of measured values of the dosimeters, read at the dosimeter service institution, and storing the measured values of the dosimeters read at the dosimeter service institution in an archive institution, wherein the dosimeter fitting wear is made of a stretchable material.

33. The body surface exposure dose distribution measuring method according to claim 32, wherein the medical institution is informed of measured values of the dosimeters as exposure dose distribution map data corresponding to measuring positions from the dosimeter service institution.

* * * * *